US009050016B2

(12) United States Patent
Zhang

(10) Patent No.: US 9,050,016 B2
(45) Date of Patent: Jun. 9, 2015

(54) SYSTEM FOR HEART PERFORMANCE CHARACTERIZATION AND ABNORMALITY DETECTION

(75) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1068 days.

(21) Appl. No.: 12/702,805

(22) Filed: Feb. 9, 2010

(65) Prior Publication Data

US 2010/0204585 A1  Aug. 12, 2010

Related U.S. Application Data

(60) Provisional application No. 61/151,318, filed on Feb. 10, 2009.

(51) Int. Cl.
| A61B 5/05 | (2006.01) |
| A61B 5/053 | (2006.01) |
| A61B 5/0452 | (2006.01) |
| A61B 5/00 | (2006.01) |

(52) U.S. Cl.
CPC .............. *A61B 5/053* (2013.01); *A61B 5/0452* (2013.01); *A61B 5/7217* (2013.01)

(58) Field of Classification Search
USPC ................................. 600/508, 509, 513, 547
See application file for complete search history.

(56) References Cited

U.S. PATENT DOCUMENTS

| 3,871,359 | A | * | 3/1975 | Pacela ........................... 600/547 |
| 5,025,784 | A | | 6/1991 | Shao et al. |
| 5,201,808 | A | | 4/1993 | Steinhaus et al. |
| 5,309,917 | A | | 5/1994 | Wang et al. |
| 5,423,326 | A | | 6/1995 | Wang et al. |
| 5,443,073 | A | | 8/1995 | Wang et al. |
| 5,794,623 | A | | 8/1998 | Forbes |
| 5,817,093 | A | | 10/1998 | Williamson et al. |
| 6,011,992 | A | | 1/2000 | Hubbard et al. |
| 6,095,987 | A | | 8/2000 | Shmulewitz |
| 6,436,049 | B1 | * | 8/2002 | Kamiyama et al. ........... 600/458 |
| 6,473,641 | B1 | | 10/2002 | Kodama |
| 6,532,384 | B1 | | 3/2003 | Fukuda |
| 6,633,777 | B2 | | 10/2003 | Szopinski |
| 6,643,543 | B2 | | 11/2003 | Takehara et al. |
| 6,807,444 | B2 | | 10/2004 | Tu et al. |
| 7,200,440 | B2 | | 4/2007 | Kim et al. |
| 7,474,918 | B2 | | 1/2009 | Frantz et al. |
| 2001/0051774 | A1 | | 12/2001 | Littrup |
| 2002/0002389 | A1 | | 1/2002 | Bradley et al. |

(Continued)

*Primary Examiner* — Paula J Stice

(57) ABSTRACT

A system for heart performance characterization receives an electrical signal indicating heart electrical activity of a patient over a heart beat cycle. The electrical signal is acquired at a particular anatomical location. A gating signal generator generates a gating signal for use in identifying a particular portion of the heart beat cycle. An acquisition device, responsive to the gating signal, derives first and second voltage potentials from the received electrical signal. The first voltage potential comprises a voltage potential derived over a time period comprising a heart beat cycle and the second voltage potential comprises a voltage potential derived over a time period comprising a particular portion of the heart beat cycle. A computation processor derives a dynamic impedance representative value by adjusting a baseline impedance value by a ratio of the first and second voltage potentials. The dynamic impedance represents an average impedance at the particular anatomical location over a time period comprising the particular portion of the heart beat cycle.

17 Claims, 6 Drawing Sheets

(56) References Cited

U.S. PATENT DOCUMENTS

| | | |
|---|---|---|
| 2002/0193689 A1 | 12/2002 | Bernstein et al. |
| 2003/0163061 A1 | 8/2003 | Miyoshi et al. |
| 2004/0006279 A1 | 1/2004 | Arad |
| 2005/0101875 A1 | 5/2005 | Semler et al. |
| 2006/0212484 A1 * | 9/2006 | Chaffin et al. ............ 707/104.1 |

* cited by examiner

SYSTEM FOR HEART PERFORMANCE CHARACTERIZATION AND ABNORMALITY DETECTION

This is a non-provisional application of provisional application Ser. No. 61/151,318 filed Feb. 10, 2009, by H. Zhang.

FIELD OF THE INVENTION

This invention concerns a system for heart performance characterization and abnormality detection involving deriving dynamic impedance representative values.

BACKGROUND OF THE INVENTION

Cardiovascular disease is a serious illness and cardiac electrophysiological signals (such as signal magnitude) are utilized to diagnose and characterize associated patient electrophysiological (EP) pathology, such as atrial fibrillation and myocardial ischemia (MI). Usually, surface ECG signal and intra-cardiac EP signal analysis based on waveform morphology and time domain parameters is utilized for cardiac arrhythmia detection and characterization as well as determination of P wave morphology changes, R-R wave time intervals and heart rate variability analysis. Some known systems employ tissue impedance based analysis and diagnosis based on temperature measurement in an ablation procedure for cardiac arrhythmia discrimination (using a thermistor), for example. However, known systems typically focus on calculation and interpretation of a single EP impedance derived in response to an external stimulation pulse. Such stimulation involves generation of electrical noise that degrades EP signals and involves current, voltage and power leakage that may impair patient safety and may degrade precision and reliability of impedance measurement and analysis.

Known signal processing systems use intra-cardiac electrograms to analyze cardiac arrhythmias, such as Atrial Fibrillation (AF) and Ventricular Fibrillation (VF), but these systems fail to determine intrinsic electrophysiological characteristics of heart tissue for more accurate and reliable diagnosis of cardiac arrhythmia, such as impedance. Known cardiac tissue or body impedance measurement systems for cardiac function diagnosis and evaluation fail to comprehensively determine tissue impedance, especially impedance changes and fail to identify cardiac disease and severity. In cardiac impedance analysis, electrophysiological signals (such as surface ECG signals, ICEG (intra-cardiac electrogram) signals) and vital signs (pressure signals, respiration signals) are typically inadequately used in impedance estimation and quantification. A system according to invention principles addresses these deficiencies and related problems.

SUMMARY OF THE INVENTION

A system determines myocardial and body tissue impedance and variation and time-varying impedance patterns to diagnose cardiac function and health status and identify cardiac disorders, characterize pathological severity, predict life-threatening events and evaluate drug delivery effects. A system for heart performance characterization and abnormality detection, includes an interface for receiving an electrical signal indicating heart electrical activity of a patient over a heart beat cycle. The electrical signal is acquired at a particular anatomical location. A gating signal generator generates a gating signal for use in identifying a particular portion of the heart beat cycle. An acquisition device, responsive to the gating signal, derives first and second voltage potentials from the received electrical signal. The first voltage potential comprises a voltage potential derived over a time period comprising a heart beat cycle and the second voltage potential comprises a voltage potential derived over a time period comprising a particular portion of the heart beat cycle. A computation processor derives a dynamic impedance representative value by adjusting a baseline impedance value by a ratio of the first and second voltage potentials. The dynamic impedance represents an average impedance at the particular anatomical location over a time period comprising the particular portion of the heart beat cycle.

DETAILED DESCRIPTION OF THE INVENTION

A system improves safety, precision and reliability of cardiac impedance measurement and calculation used in diagnosis, by analyzing and characterizing tissue impedance changes based on cardiac electrophysiological waveforms, such as surface ECG signals and intra-cardiac electrograms. The system utilizes signal morphology, frequency and power information to quantify body tissue impedance as well as to characterize time-varying patterns and mode of the impedance. The system calculates and interprets myocardial and body tissue impedance and variation to determine cardiac function and health status and identify cardiac disorders, characterize pathological severity, predict life-threatening events and evaluate drug delivery effects. Further, the system provides cardiac function interpretation by analysis of signal morphology, frequency and power information to quantify tissue and body impedance. The performed signal analysis comprises magnitude and frequency analysis, and involves use of determined characteristics, including signal shape, waveform morphology, power, spectrum, signal pattern and mode, to calculate the impedance changes.

The heart behaves as a power source, which is stable for individual heart beat cycles but pathology may impact tissue characteristics which results in electrophysiological changes, such as impedance changes. Consequently, electrical current or voltage generated in a heart changes as a result of impedance variation. The system uses monitored voltage and signals in calculation to localize and diagnose impedance change and cardiac pathology. Tissue impedance is a dynamic electrophysiological parameter and varies with time. Impedance change due to the cardiac pathology may only happen in a specific portion in a heart cycle ECG signal, such as during an ST segment portion during a myocardial ischemia event or during a P wave portion in the case of atrial fibrillation, for example. The system dynamically monitors impedance change to identify an impedance pattern, mode and time varying changes in different portions of a cardiac cycle.

Figure 1:
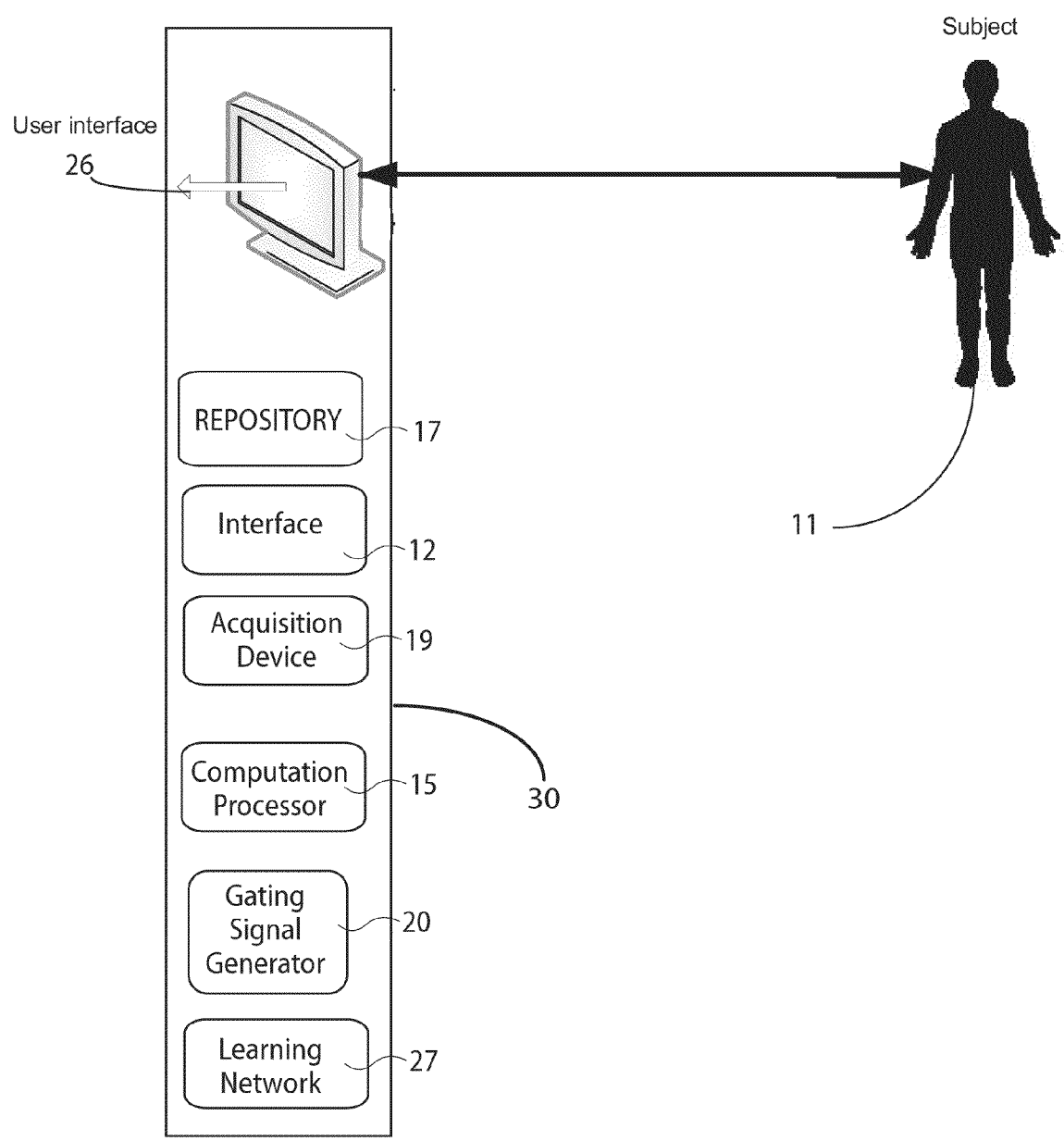
FIG. 1 shows a system for heart performance characterization and abnormality detection, according to invention principles.

FIG. 1 shows a system 10 for heart performance characterization and abnormality detection. System 10 comprises at least one computer system, workstation, server or other processing device 30 including interface 12, repository 17, acquisition device 19, computation processor 15, gating signal generator 20, learning network 27 and a user interface 26. Interface 12 receives an electrical signal indicating heart electrical activity of patient 11 over a heart beat cycle acquired at a particular anatomical location. Gating signal generator 20 generates a gating signal for use in identifying a particular portion of the heart beat cycle and acquisition device 19, responsive to the gating signal, derives first and second voltage potentials from the received electrical signal. The first voltage potential comprises a voltage potential derived over a time period comprising a heart beat cycle and the second voltage potential comprises a voltage potential derived over a time period comprising a particular portion of the heart beat cycle. Computation processor 15 derives a dynamic impedance representative value by adjusting a baseline impedance value by a ratio of the first and second voltage potentials and stores the dynamic impedance value in repository 17. The dynamic impedance represents an average impedance at the particular anatomical location over a time period comprising the particular portion of the heart beat cycle. Self learning network (e.g., an Artificial Neural Network (ANN)) 27 employs training datasets for deriving a correction factor for determining a normalized absolute value for the dynamic impedance. Further, computation processor 15 generates a health status indicator presented on user interface 26 by multiplying the dynamic impedance by the derived correction factor to determine a normalized value for the dynamic impedance.

Learning network 27 employs nonlinear modeling to determine and characterize nonlinear relationships between EP and vital sign signals (including magnitude, morphology, mode, pattern and power characteristics of the signals) as well as cardiac impedance characteristics. The nonlinear modeling and analysis may comprise an ANN system, Fuzzy analysis system or expert system, for example. In addition, system 10 analyzes a combination of patient parameters and vital signs signals (respiration) and hemodynamic signals (NIBP), in interpretation of cardiac impedance and function and uses signal synchronization to eliminate noise and signal distortions, from calculation. System 10 provides real time multichannel intra-cardiac dynamic impedance analysis and pattern analysis of cardiac tissue and heart circulation and extracts impedance information which may later manifest as ECG signal morphology changes or ICEG (intra-cardiac electrogram) signal changes.

System 10 uses tissue electrophysiological characteristics, such as patient intracardiac electrical impedance, for detection, diagnosis and characterization of cardiac arrhythmia and heart tissue malfunctions, health status estimation and quantification. Cardiac tissue and body impedance and specifically variation of local cardiac tissue impedance have an intrinsic relationship with cardiac disease such as myocardial ischemia. Cardiac arrhythmias are usually related to tissue abnormality and variation in electrophysiological characteristics. For example, if there is a reentrant mechanism occurring within an atrium, typically electrical excitation conduction may be affected and result in partial electrophysiological changes, such as partial signal excitation and propagation blockage, which means the electrophysiological impedance characteristics of the local tissue within the atrium have changed. A reentrant mechanism involves two different conduction pathways, either anatomical or functional and unidirectional block in one pathway. This allows an impulse traveling down one pathway to re-enter the other pathway and return to the original site and travel down the original pathway. This is known as circus movement or re-entry. Re-entry is a common mechanism for tachycardias.

Figure 2:
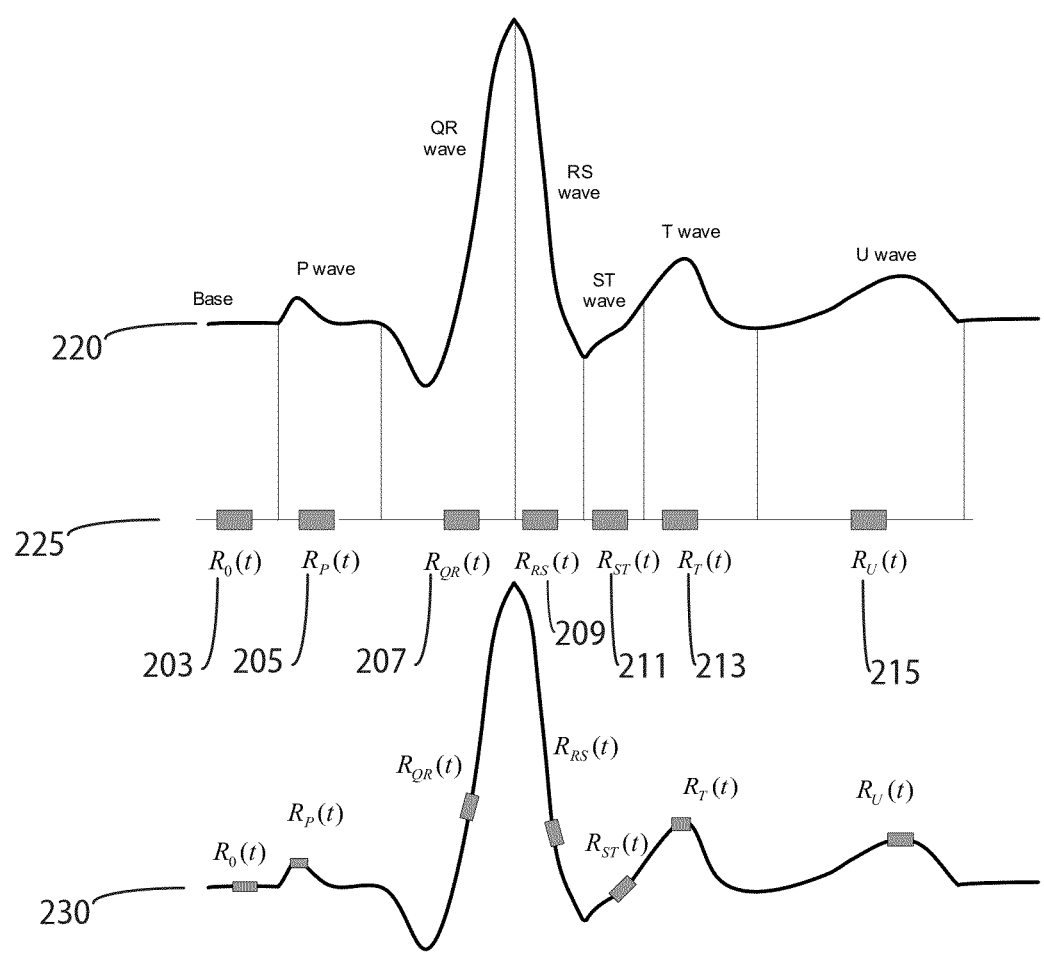
FIG. 2 shows an electrophysiological equivalent impedance modeling and mapping of different stages of a cardiac cycle and cardiac function, according to invention principles.

FIG. 2 shows electrophysiological equivalent impedance modeling and mapping of different stages of a cardiac cycle and cardiac function. Specifically, FIG. 2 shows an electrophysiological signal (ECG or ICEG) 220, corresponding equivalent impedance chart 225 and electrophysiological waveform model 230 with superimposed representative impedance. A cardiac cycle is analyzed using different kinds of cardiac function stages. The cardiac cycle depicts changes in aortic pressure (AP), left ventricular pressure (LVP), left atrial pressure (LAP), left ventricular volume (LV Vol), and heart sounds during a single cycle of cardiac contraction and relaxation. These changes are related in time to an electrocardiogram. A single cycle of cardiac activity may be divided into stages including, a first stage comprising a diastole stage, which represents ventricular filling and a brief period just prior to filling at which time the ventricles are relaxing. A second stage comprises a systole stage which represents the time of contraction and ejection of blood from the ventricles. A cardiac cycle is usually divided into seven phases for analyzing the diastole and systole stages in more detail. A first phase begins with a P wave of the electrocardiogram, which represents atrial depolarization. The last phase of the cardiac cycle ends with appearance of a next P wave.

The different phases of a cardiac cycle comprise, Phase 1—Atrial Contraction, Phase 2—Isovolumetric Contraction, Phase 3—Rapid Ejection, Phase 4—Reduced Ejection, Phase 5—Isovolumetric Relaxation, Phase 6—Rapid Filling and Phase 7—Reduced Filling. System 10 (FIG. 1) uses cardiac dynamic impedance indicating electrophysiological response and characteristics, to divide a cardiac cycle into 7 electrophysiological portions or stages. These stages include, a P wave dynamic impedance 205, a QR wave dynamic impedance 207, an RS wave dynamic impedance 209, an ST wave dynamic impedance 211, a T wave dynamic impedance 213, a U wave dynamic impedance 215 and a Rest time base impedance $R_0(t)$ 203. For an individual electrophysiological stage, a dynamic impedance $R_i(t)$ representing electrophysiological variation is an impedance on top of a base impedance $R_0(t)$, which is the static part of the cardiac tissue impedance through a cardiac cycle. Hence the cardiac impedance of the each stage is $R_0(t)+R_i(t)$. Electrophysiological waveform model 230 shows equivalent impedance modeling based on cardiac electrophysiological characteristics, that is utilized for detection, diagnosis and evaluation of cardiac pathologies and malfunctions, by use of $R_P(t)$ (P wave segment impedance) for atrial fibrillation and (ST segment impedance) $R_{ST}(t)$ for myocardial ischemia.

The dynamic impedance and variation of an individual stage in the cardiac cycle is used to analyze and capture electrophysiological characteristic changes. An impedance includes: 1) an absolute value of the cardiac electrophysiological impedance and 2) a change of the electrophysiological impedance which may be more significant for cardiac tissue and function characterization. The change may comprise a variation or deviation percentage derived by high order statistical analysis, such as standard deviation or bi-spectrum analysis, for example. A heart self pacing and contraction mechanism may be treated as a power source and tissue impedance system as shown in FIG. 2. Further, the heart power is time varying and periodic (per cardiac cycle) and power (voltage and current) follows a particular heart pacing and control sequence, which governs blood and tissue during depolarization and repolarization, corresponding to a contraction and reperfusion mechanism in a heart and circulation system.

Figure 3:
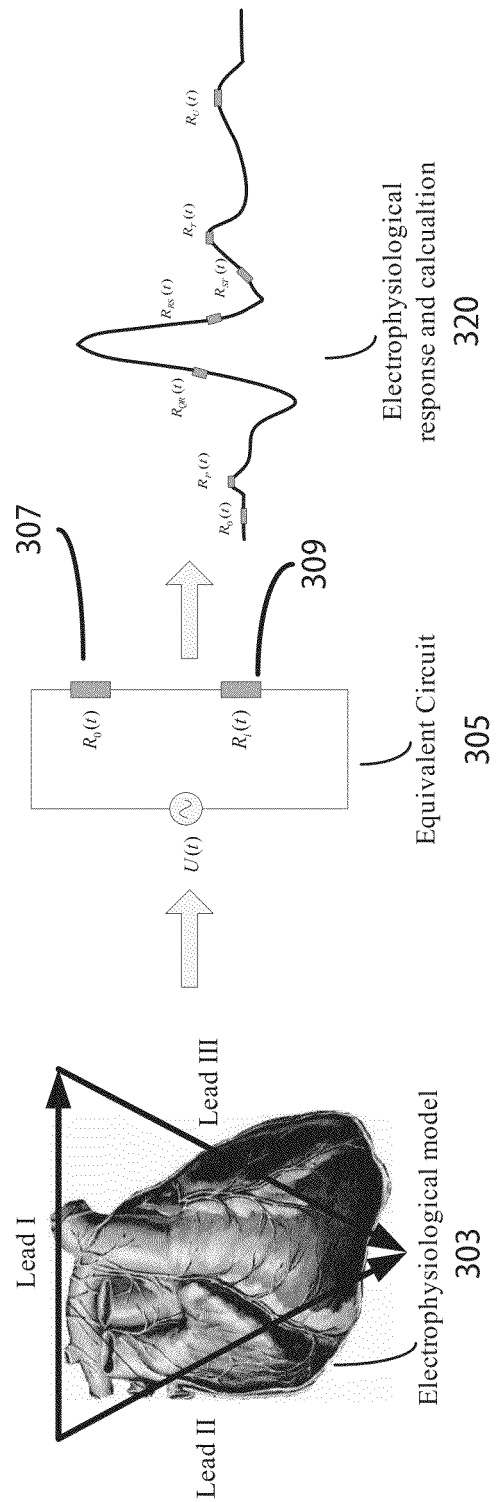
FIG. 3 shows a heart system and corresponding equivalent electrical circuit model, according to invention principles.

FIG. 3 shows a heart system and corresponding equivalent electrical circuit model. A heart control and contraction system 303 is mapped to circuit. U(t) 305 representing an equivalent power system (including a voltage and current source) for pacing, contracting and other electrophysiological activities. $R_0(t)$ 307 and $R_i(t)$ 309 are equivalent electrical impedances for the cardiac tissue and circulation system. U(t) 305 periodically excites and controls cardiac tissue $R_0(t)$ and $R_i(t)$ to fulfill cardiac depolarization, repolarization and other electrophysiological stages. Based on the equivalent modeling and pattern of the cardiac system, the dynamic impedance $R_i(t)$ is determined as illustrated in waveform 320. According to electrophysiological characteristics, the base impedance $R_0(t)$ is usually a stable value over a cardiac cycle and is replaced by an average or mean impedance (for each cardiac cycle), $R_{mean}$, for simplification of the calculation and dynamic evaluation procedure. Hence the voltage across the base impedance $R_{mean}$ linearly corresponds to baseline cardiac signals since $R_{mean}$ does not change abruptly (in time and frequency domain parameters, such as magnitude, latency, peaks, power). Also pathology and malfunction related signal (voltage and current) changes (distortion, variation) mainly manifest in the dynamic impedance part: $R_i(t)$.

A current through $R_0(t)$ is the same as through $R_i(t)$. Hence $$\frac{U_0(t)}{R_0(t)} = \frac{U_i(t)}{R_i(t)} \text{ or}$$

Dynamic impedence calculation: $R_i(t) = R_0(t) \cdot \frac{U_i(t)}{U_0(t)}$ in which, $U_0(t)$ and $U_i(t)$ represent voltage across impedance $R_0(t)$ and $R_i(t)$ respectively (the data here is from signal potentials which may be derived from discrete calculation for an individual sample in a heart cycle stage). Using the equation, $R_i(t)$ is derived using baseline signals, which are utilized for $R_{ST\_base}(t)$ calculation, estimation and characterization. The baseline dynamic value is used for real time dynamic impedance calculation and monitoring.

The signal morphology (and other signal parameters, such as frequency, power, spectrum) changes are utilized to estimate the value and variation of tissue dynamic impedance. For example, in a stent installation procedure (such as in the Left Anterior Descending Artery (LAD)), a dynamic impedance of a corresponding lead signal is utilized to capture changes in an ST segment (and RS wave). The ST segment based dynamic impedance is calculated as follows (here the continuous version is shown and the data can be discrete when real time digitization and calculation is performed):

$$\text{Absolute value: } R_{ST}(t) = \alpha \cdot R_{ST\_base}(t) \frac{U_{ST}(t)}{U_{ST\_base}(t)}$$

$$\text{Variation and deviation: } \nabla_{ST}(t) = \|R_{ST}(t) - R_{ST\_base}(t)\| \text{ or}$$

$$\mu_{ST}(t) = \frac{\|R_{ST}(t) - R_{ST\_base}(t)\|}{\|R_{ST\_base}(t)\|}$$

In the above equations, $R_{ST}(t)$ represents the absolute value of the measured dynamic impedance and $R_{ST\_base}(t)$ represents the dynamic impedance of the ST segment stage in baseline signals, $\alpha$ is a linear or nonlinear coefficient between dynamic impedances of different stages (which can be derived empirically). In one implementation, $\alpha$=0.975. Further, $\alpha$ may be a slow time varying parameter and may be adjusted adaptively). $\nabla_{ST}(t)$ and $\mu_{ST}(t)$ represent variation values (such as ohms) and relative deviation or signal change percentage.

The number of samples in a heart cycle used for calculation affects accuracy of calculation of dynamic impedance. For example, if there are 100 data sample points in an ST segment, a smooth $R_{ST}(t)$ waveform is generated. Otherwise, the calculation resolution is limited. Computation processor 15 derives a waveform of $R_{ST}(t)$, $\nabla_{ST}(t)$ and $\mu_{ST}(t)$ and uses it to determine pathology (cardiac arrhythmia or events) and health status of a patient. For example, in an ST segment calculation processor 15 determines a health index value and the closer the health index value is to 1, the better the patient health status is. Processor 15 adaptively selects a type of health index calculation in response to a type of clinical application and diagnosis being performed. The health index calculation is applied to different portions in a cardiac cycle associated signal.

Processor 15 calculates an average health index, $$\text{Health\_index} = 1 - \frac{1}{N} \sum_{i \in ST} \|\mu_{ST}(i)\|,$$

where N is the number of samples in an ST segment.

Processor 15 calculates a maximum health index, $$\text{Health\_index} = 1 - \underset{i \in ST}{\text{MAX}} \|\mu_{ST}(i)\|$$

The dynamic impedance calculation for an ST segment is used by processor 15 to interpret and characterize myocardial ischemia events in a stent installation in a LAD. Dynamic impedance evaluation and quantification is similarly performed in other portions of a cardiac cycle, such as during a P wave or RS stage, for example. The system 10 dynamic impedance measurement, interpretation and characterization is utilized in real time monitoring and diagnosis during a clinical procedure and for prediction of life-threatening event and drug delivery effects. The dynamic impedance at a particular cardiac stage is not a static value, but a waveform. System 10 advantageously performs pattern and mode analysis of dynamic impedance in identifying cardiac pathology and quantifying clinical events for small signal changes. Furthermore, system 10 uses calculated dynamic impedance together with other parameters associated with cardiac signal power, frequency, instantaneous frequency, complexity and spectrum, in dynamically mapping parameter values to candidate medical conditions using predetermined mapping information.

Computation processor 15 applies bandwidth analysis to calculated dynamic impedance to determine signals in a frequency band $f_1$-$f_2$ (for example, 20-40 Hz). Processor 15 uses a filter to perform an analysis in a region of interest (ROI).

Computation processor 15 calculates an Absolute value, $$R_{ST(f_1-f_2)}(t) = \alpha \cdot R_{ST\_base(f_1-f_2)}(t) \frac{U_{ST(f_1-f_2)}(t)}{U_{ST\_base(f_1-f_2)}(t)}$$

Computation processor 15 also calculates variation and deviation, $$\nabla_{ST(f_1-f_2)}(t) = \|R_{ST(f_1-f_2)}(t) - R_{ST\_base(f_1-f_2)}(t)\| \text{ or}$$

$$\mu_{ST(f_1-f_2)}(t) = \frac{\|R_{ST(f_1-f_2)}(t) - R_{ST\_base(f_1-f_2)}(t)\|}{\|R_{ST\_base(f_1-f_2)}(t)\|}$$

An ST segment is used for dynamic impedance calculation in the frequency band $f_1$-$f_2$ in the previous calculations but this is exemplary only. The calculations may be applied to any portions in a heart cycle.

System 10 employs learning network 27 comprising a nonlinear diagnosis, test and decision system for dynamic impedance calculation, characterization and health status determination. The calculation and estimation of dynamic impedance may be sensitive to noise, such as temperature change, respiration, patient movement and other patient noise. Additionally coefficient α may vary between patients. The sources of nonlinearity and uncertainty are reduced using nonlinear modeling provided by learning network 27 comprising an artificial neural network (ANN), Fuzzy algorithm or expert system, for example.

Figure 4:
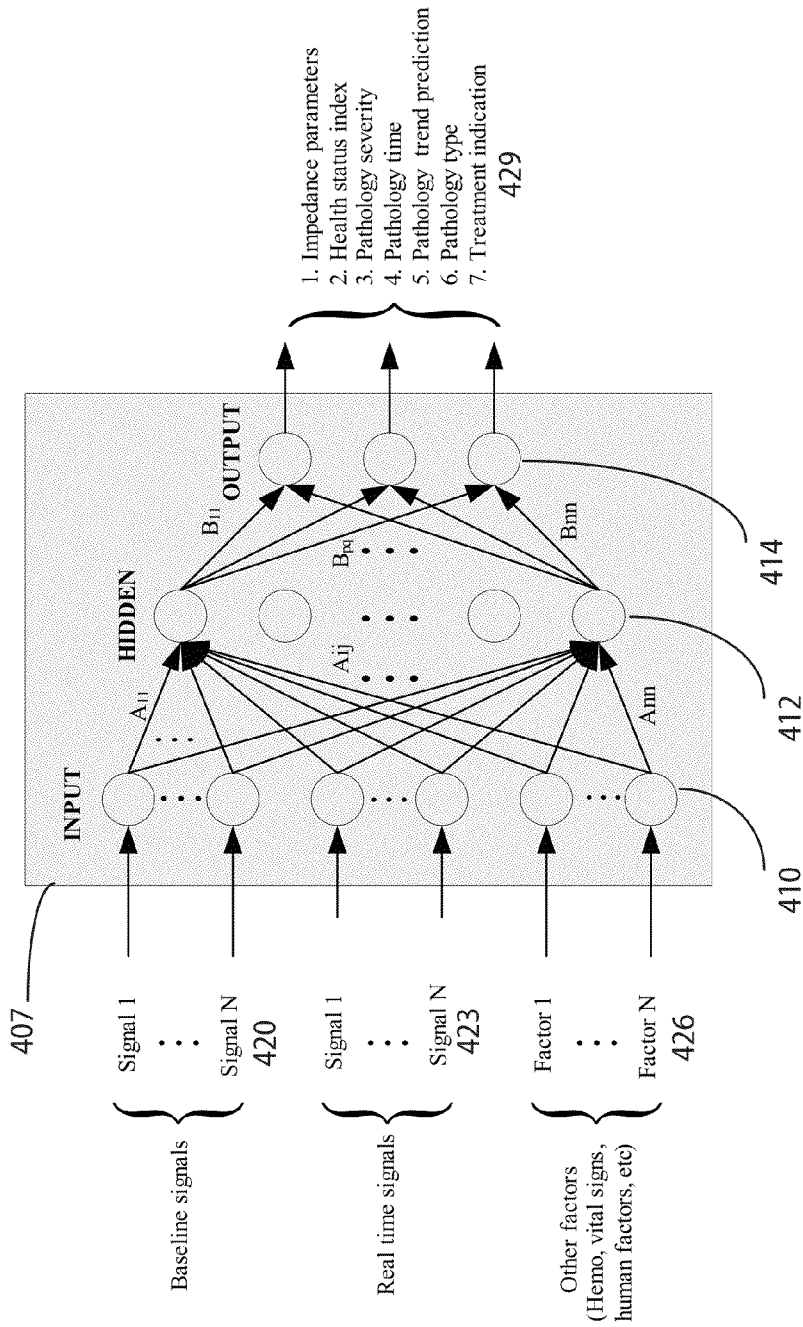
FIG. 4 shows an artificial neural network (ANN) system for cardiac dynamic impedance calculation and health status analysis and characterization, according to invention principles.

FIG. 4 shows artificial neural network (ANN) system 407 employed by learning network 27 (FIG. 1) for cardiac dynamic impedance and health index calculation and health status analysis and characterization. ANN unit 407 provides a nonlinear function including noise compensation and analysis using training data and related factors. ANN 407 estimates heart impedance parameter values and candidate patient medical condition by determining a nonlinear relationship between heart and vital sign signal data and corresponding training data derived from a patient population having demographic characteristics of the patient (e.g., age, gender, height, weight, pregnancy status) processed by ANN 407.

ANN unit 407 maps one or more real time electrophysiological signals (e.g., ECG and ICEG signals) 423, corresponding baseline signals 420 derived from patient population and hemodynamic signals, vital sign signals and human factors 426 to output parameters 429. Output parameters 429 include impedance parameters, a patient health status index, pathology severity indicator, a time of a cardiac event, a pathology trend indication, a pathology type indication and candidate treatment suggestions. Signal 1 to signal N correspond to different cardiac cycle stages, different frequency bandwidths or different parameters, for example, and are adaptively selected in response to data identifying a clinical application and clinical usage. ANN unit 407 structure comprises 3 layers, an input layer 410, hidden layer 412 and output layer 414. ANN unit $A_{ij}$ weights are applied between input layer 410 and hidden layer 412 components of the ANN computation and $B_{pq}$ weights are applied between hidden layer 412 and calculation index components 414 of the ANN computation. The $A_{ij}$ weights and $B_{pq}$ weights are adaptively adjusted and tuned using a training data set. ANN unit 407 incorporates a self-learning function that processes signals 420, 423 and 426 to increase the accuracy of calculated results. ANN unit 407 maps determined impedance parameters and input signals 420, 423 and 426 to a candidate diagnosis or treatment suggestion 429 to localize a tissue impairment within an organ and determine time of occurrence within a heart cycle. ANN unit 407 also identifies arrhythmia type (e.g., AF, MI, VT, VF), severity of arrhythmia treatment and urgency level and is usable for automatic heart condition detection, diagnosis, warning and treatment. Further unit 407 performs statistical analysis to construct a threshold used to detect tissue impairment and diagnose and predict cardiac arrhythmia and pathology.

Following a training phase with a training data set, ANN unit 407 maps signals 420, 423 and 426 to data 429 indicating an Arrhythmia type, Arrhythmia severity, candidate treatment suggestions, localized tissue impairment information identifying the cardiac arrhythmia position, pathology conducting sequence, abnormal tissue area and focus of the disorder and irregularity, for example. System 10 analyzes cardiac electrophysiological signals (including ECG and internal cardiac electrograms) based on predetermined mapping information to identify cardiac disorders, differentiate cardiac arrhythmias and quantitative and qualitative analysis and characterization of cardiac pathology and events. The severity threshold of a pathology mapping decision may vary from person to person and is adjusted at the beginning of analysis and in one embodiment may be dynamically adjusted in response to a signal quality or noise measurement, for example. The system may be advantageously utilized in general patient monitoring and implantable cardiac devices for real time automatic analysis and detection of cardiac arrhythmias and abnormalities. The cardiac dynamic impedance estimation in one embodiment uses different kinds of hypothesis test for medical condition detection decisions, such as a T test, that can be used by ANN unit 407 to improve sensitivity and characterization of cardiac dynamic impedance.

Figure 5:
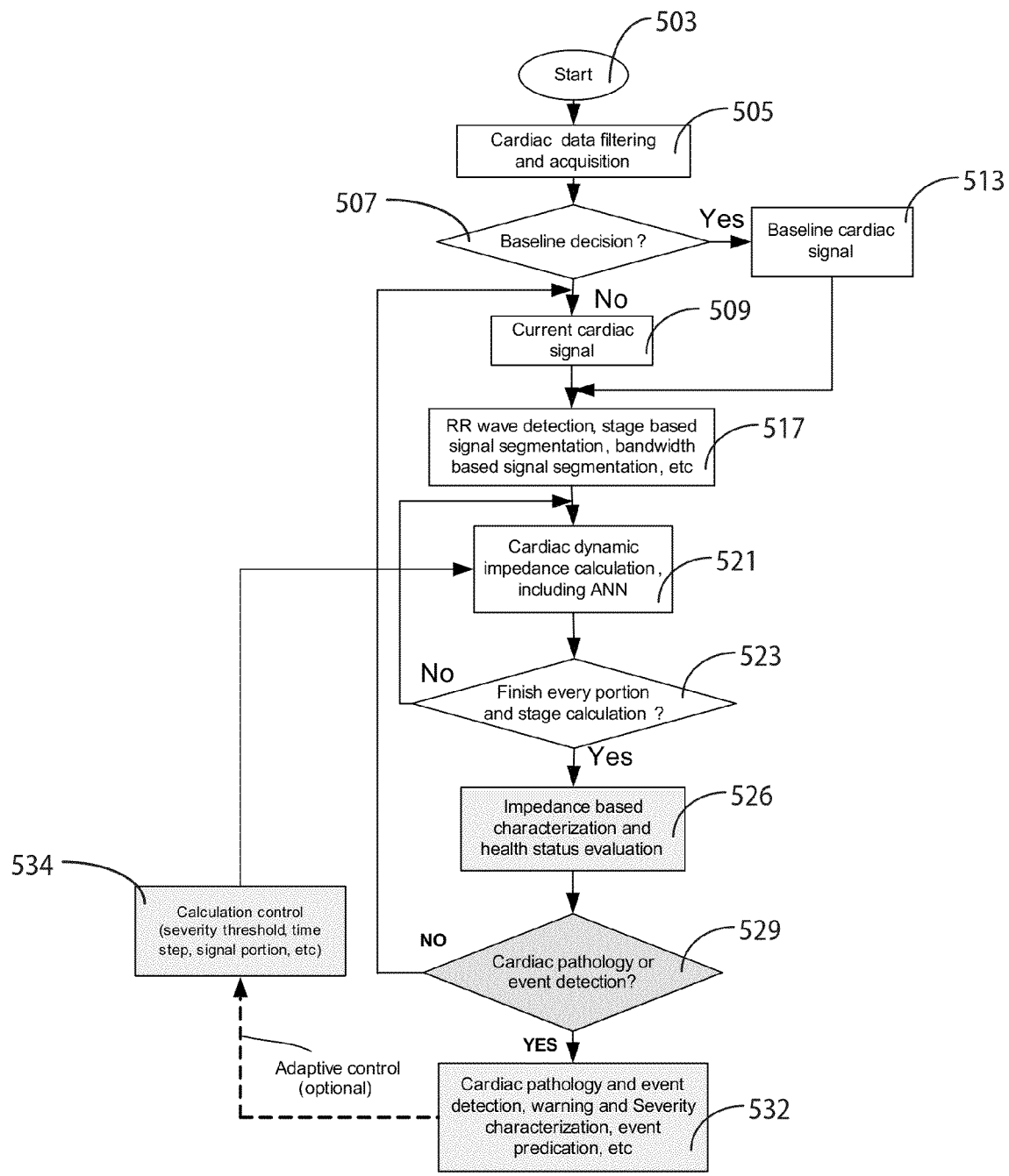
FIG. 5 shows a flowchart of a process for cardiac dynamic impedance determination and analysis, according to invention principles.

FIG. 5 shows a flowchart of a process for cardiac dynamic impedance determination and analysis used by system 10 (FIG. 1). In step 505 following the start at step 503, system 10 acquires and filters cardiac electrophysiological signal data and in step 507 determines if acquired signal data comprises baseline data of the signal and if so identifies a baseline value of the signal in step 513. If acquired signal data is not baseline data, it is identified as cardiac signal data in step 509 and pre-analyzed by acquisition device 19 in step 513. Acquisition device 19 in step 517 processes the cardiac signal data to detect a QRS complex (RR wave) and identify cardiac cycle segments including P wave, QR wave, RS wave, ST segment, T wave and U wave segments. Device 19 also detects individual cardiac cycle segments in the cardiac signal data based on bandwidth. Acquisition device 19 in response to a gating signal, derives first and second voltage potentials in the cardiac signal data. The first voltage potential comprises a voltage potential derived over a time period substantially comprising a heart beat cycle and the second voltage potential comprises a voltage potential derived over a time period comprising a particular portion of a heart beat cycle. In step 517 computation processor 15 performs real time data based cardiac dynamic impedance calculation. In one embodiment system 10 uses ANN unit 407 to perform nonlinear calculation and noise compensation. Computation processor 15 in step 521 derives a dynamic impedance representative value by adjusting a baseline impedance value by a ratio of the first and second voltage potentials. The baseline impedance value represents an averaged impedance of cardiac tissue at the particular anatomical location over a time period comprising a heart beat cycle. The dynamic impedance represents an average impedance at the particular anatomical location over a time period comprising the particular portion of the heart beat cycle.

In step 523, acquisition device 19 and computation processor 15 derives a dynamic impedance representative value and a health index value for the individual segments of a cardiac cycle. Steps 521 and 523 are iteratively repeated until calculation for the different stages of a heart cycle is completed. In step 526, computation processor 15 identifies a particular medical condition by mapping determined dynamic impedance values and health index values as well as the other patient parameter values to corresponding value ranges associated with medical conditions using predetermined mapping information stored in repository 17. Upon a determination of good health condition in step 526, processor 15 in step 529 iteratively repeats performance of steps 509, 517, 521, 523, 526 and 529 as a continuous real-time patient process for monitoring and diagnosis of cardiac conditions. In response to a determination of a cardiac event or pathology in step 526, processor 15 in step 529 initiates generation of an alert message in step 532 indicating further actions, tests and treatments for the detected cardiac pathology and event. The actions include adaptive control and adjustment of parameters governing dynamic impedance and health index value calculation in step 534. The parameters controlled include a severity (warning) threshold, calculation time step and a particular signal portion to be averaged which are determined by user input or adaptive adjustment by an executable application.

Figure 6:
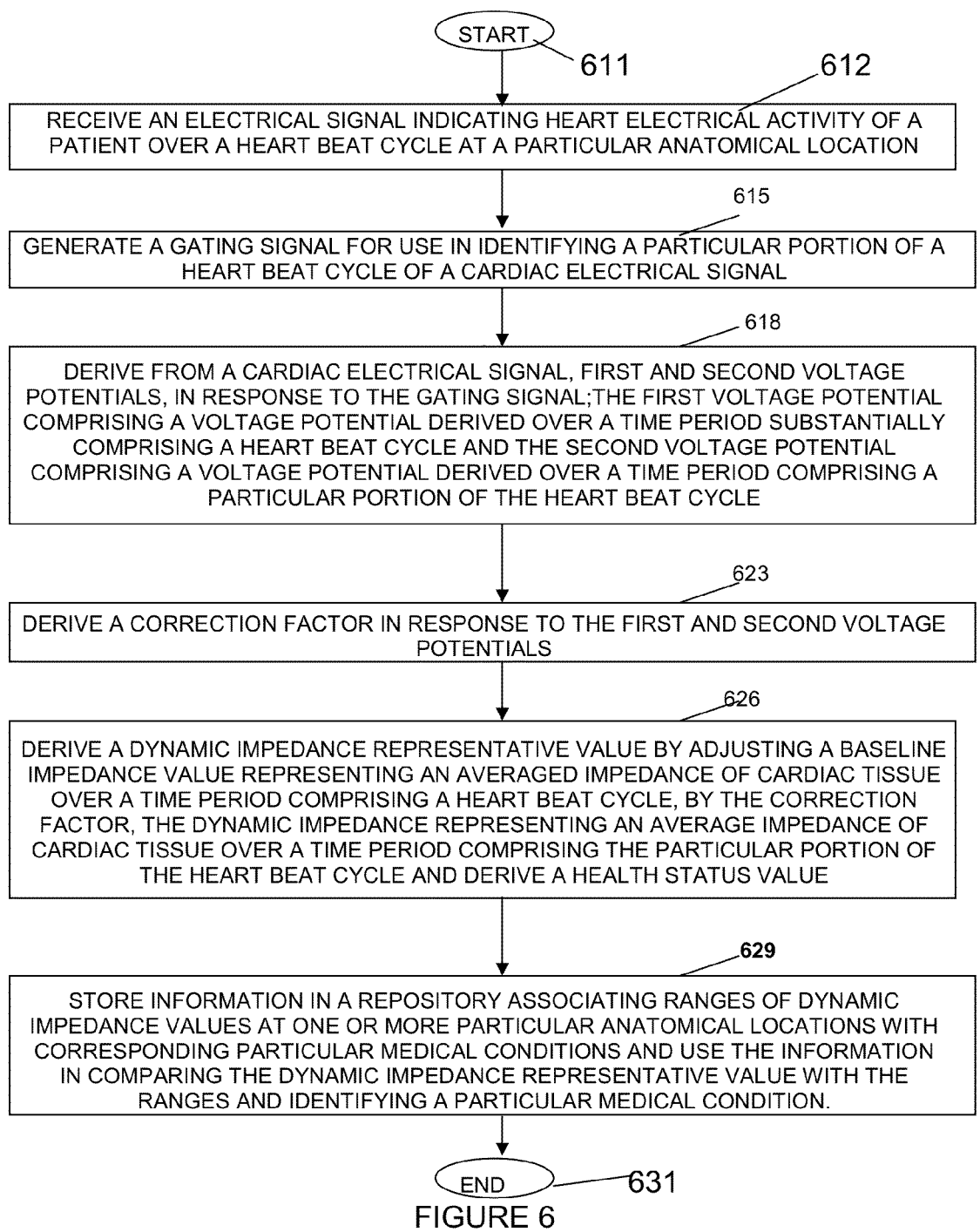
FIG. 6 shows a flowchart of a process used by a system for heart performance characterization and abnormality detection, according to invention principles.

FIG. 6 shows a flowchart of a process used by system 10 (FIG. 1) for heart performance characterization and abnormality detection. Interface 12 in step 612 following the start at step 611, receives a cardiac electrical signal indicating heart electrical activity of a patient over a heart beat cycle that is acquired at a particular anatomical location. Gating signal generator 20 in step 615 generates a gating signal for use in identifying a particular portion of a heart beat cycle of the cardiac electrical signal. In step 618 acquisition device 19 derives from the cardiac electrical signal, first and second voltage potentials (or first and second electrical currents), in response to the gating signal. The first voltage potential comprises a voltage potential derived over a time period substantially comprising a heart beat cycle and the second voltage potential comprises a voltage potential derived over a time period comprising a particular portion of the heart beat cycle. Acquisition device 19 derives the first value representing the first voltage potential by averaging a voltage potential over a time period comprising one or more heart beat cycles and derives the second value representing the second voltage potential by averaging a voltage potential over a time period comprising the particular portion of one or more heart beat cycles.

Device 19 in step 623 derives a correction factor comprising a ratio of the first and second voltage potentials in one embodiment, in response to the first and second voltage potentials. In step 626, computation processor 15 derives a dynamic impedance representative value by adjusting a baseline impedance value representing an averaged impedance of cardiac tissue over a time period comprising a heart beat cycle, by the correction factor. Computation processor 15 derives the baseline impedance value by averaging received measured cardiac tissue impedance values at the particular anatomical location over a time period comprising a heart beat cycle, in response to received measured voltage potential and current values over the heart beat cycle. The dynamic impedance represents an average impedance of cardiac tissue over a time period comprising the particular portion of the heart beat cycle. In one embodiment, computation processor derives the dynamic impedance representative value using a function of the form $$R_i(t) = R_0(t) \cdot \frac{U_i(t)}{U_0(t)}$$

where, $U_0(t)$ and $U_i(t)$ represent average voltage potentials across impedance $R_0(t)$ and $R_i(t)$ respectively and $R_0(t)$ is the baseline impedance value and $R_i(t)$ is the dynamic impedance. Computation processor 15 compares the dynamic impedance representative value obtained on a first occasion with a corresponding dynamic impedance representative value of the patient determined at the particular anatomical location on a second occasion. The first and second occasions are at least one of, (a) pre and post treatment and (b) different hospital visits.

Computation processor 15 generates a health status indicator by multiplying the dynamic impedance by a predetermined correction factor to determine a normalized value for the dynamic impedance and the predetermined correction factor is derived from empirical measurement. In one embodiment, the predetermined correction factor is derived from at least one of, (a) patient specific empirical measurement and (b) empirical measurements from patients having patient substantially compatible age, gender, height and weight characteristics. Computation processor 15 generates a health status indicator representing dynamic variation in dynamic impedance by subtracting the baseline impedance from the dynamic impedance. Computation processor monitors a patient by substantially continuously deriving the dynamic impedance representative value.

In one embodiment, self learning network 27 employs training datasets for deriving a correction factor for determining a normalized absolute value for the dynamic impedance and generates a health status indicator by multiplying the dynamic impedance by the derived correction factor to determine a normalized value for the dynamic impedance. In step 629, computation processor 15 stores information in repository 17 associating multiple ranges of dynamic impedance values at one or more particular anatomical locations with corresponding particular medical conditions. Computation processor 15 uses the information in comparing the dynamic impedance representative value with the ranges and in identifying a particular medical condition. The process of FIG. 6 terminates at step 631.

A processor as used herein is a device for executing stored machine-readable instructions for performing tasks and may comprise any one or combination of; hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-6 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The cardiac dynamic impedance estimation is usable with surface ECG signals and other kinds of electrophysiological signals including ICEG signals (intra-cardiac electrograms). The cardiac dynamic impedance estimation and patient health status characterization is applicable to pacemaker and cardiac implantable device for measurement and characterization for patient cardiac pathology and arrhythmia (by using ICEG signals). Further, the processes and applications may, in alternative embodiments, be located on one or more (e.g., distributed) processing devices on a network connecting the elements of FIG. 1. Any of the functions and steps provided in FIGS. 1-6 may be implemented in hardware, software or a combination of both.

What is claimed is:

1. A system for heart performance characterization and abnormality detection, comprising:
    an interface conditioned for receiving an electrical signal indicating heart electrical activity of a patient over a heart beat cycle, said electrical signal being acquired at a particular anatomical location;
    a gating signal generator conditioned for generating a gating signal to identifying a particular portion within said heart beat cycle, wherein the heart beat cycle comprises more than one individual phase, and the particular portion is one of the phases of the heart beat cycle;
    an acquisition device, responsive to said gating signal, conditioned for deriving from the received electrical signal, first and second voltage potentials,
        the first voltage potential comprising a voltage potential derived over a time period substantially comprising a heart beat cycle and
        the second voltage potential comprising a voltage potential derived over a time period comprising the particular portion within said heart beat cycle, said particular portion being selected for a type of health index calculation; and
    a computation processor conditioned for deriving a dynamic impedance representative value by adjusting a baseline impedance value by a ratio of the first and second voltage potentials, said dynamic impedance configured to represent an average impedance at said particular anatomical location over a time period comprising said particular portion within said heart beat cycle.

2. The system according to claim 1, wherein
said computation processor adaptively selects said calculation type in response to a type of clinical application or diagnosis being performed and
said baseline impedance value represents an averaged impedance of cardiac tissue at said particular anatomical location over a time period comprising a heart beat cycle.

3. The system according to claim 2, wherein
said computation processor derives said baseline impedance value by averaging a received measured tissue impedance value over said heart beat cycle.

4. The system according to claim 2, wherein
said computation processor derives said baseline impedance value in response to received measured voltage potential and current values over said heart beat cycle.

5. The system according to claim 1, wherein
the first and second voltage potentials comprise first and second electrical currents and
said baseline impedance value represents an averaged impedance of cardiac tissue at said particular anatomical location over a time period comprising a heart beat cycle.

6. The system according to claim 1, wherein
said acquisition device derives the first value representing said first voltage potential by averaging a voltage potential over a time period comprising one or more heart beat cycles and
said acquisition device derives the second value representing said second voltage potential by averaging a voltage potential over a time period comprising the particular portion of one or more heart beat cycles.

7. The system according to claim 1, wherein
said computation processor derives said dynamic impedance representative value using a function of the form $$R_i(t) = R_0(t) \cdot \frac{U_i(t)}{U_0(t)}$$

where, $U_o(t)$ and $U_i(t)$ represent average voltage potentials across impedance $R_o(t)$ and $R_i(t)$ respectively and $R_o(t)$ is said baseline impedance value and $R_i(t)$ is said dynamic impedance.

8. The system according to claim 1, wherein
said computation processor generates a health status indicator by multiplying said dynamic impedance by a predetermined correction factor to determine a normalized value for said dynamic impedance, said predetermined correction factor being derived from empirical measurement.

9. The system according to claim 8, wherein
said predetermined correction factor being derived from at least one of, (a) patient specific empirical measurement and (b) empirical measurements from patients having patient substantially compatible age, gender, height and weight characteristics.

10. The system according to claim 8, wherein
said computation processor generates a health status indicator representing dynamic variation in dynamic impedance by subtracting said baseline impedance from said dynamic impedance.

11. The system according to claim 1, wherein
said computation processor monitors a patient by substantially continuously deriving said dynamic impedance representative value.

12. The system according to claim 1, wherein
said computation processor compares said dynamic impedance representative value obtained on a first occasion with a corresponding dynamic impedance representative value of the patient determined at said particular anatomical location on a second occasion.

13. The system according to claim 12, wherein
said first and second occasions are at least one of, (a) pre- and post treatment and (b) different hospital visits.

14. The system according to claim 1, including
a repository of information associating a plurality of ranges of dynamic impedance values at one or more particular anatomical locations with corresponding particular medical conditions wherein
said computation processor uses said information in comparing said dynamic impedance representative value with said ranges and identifying a particular medical condition.

15. The system according to claim 1, including
a self learning network,
employing training datasets for deriving a correction factor for determining a normalized absolute value for said dynamic impedance and
generating a health status indicator by multiplying said dynamic impedance by the derived correction factor to determine a normalized value for said dynamic impedance.

16. The system according to claim 1, wherein the computation processor is conditioned to select the type of health index calculation and derive a health index value for the particular portion using the dynamic impedance representative value.

17. The system according to claim 16, wherein the computation processor is further-conditioned to identify a particular medical condition by mapping dynamic impedance values and health index values to corresponding value ranges associated with medical conditions.

\* \* \* \* \*